United States Patent
Klessig et al.

(10) Patent No.: US 6,765,128 B1
(45) Date of Patent: Jul. 20, 2004

(54) METHOD OF USING A PATHOGEN-ACTIVATABLE MAP KINASE TO ENHANCE DISEASE RESISTANCE IN PLANTS

(75) Inventors: Daniel F. Klessig, Ithaca, NY (US); Shugun Zhang, Columbia, MO (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 09/623,034

(22) PCT Filed: Feb. 23, 1999

(86) PCT No.: PCT/US99/03882

§ 371 (c)(1),
(2), (4) Date: Aug. 24, 2000

(87) PCT Pub. No.: WO00/43796

PCT Pub. Date: Sep. 2, 1999

Related U.S. Application Data

(60) Provisional application No. 60/075,685, filed on Feb. 24, 1998.

(51) Int. Cl.[7] ........................... C12N 15/82; C12N 15/90
(52) U.S. Cl. ....................................... 800/279; 800/301
(58) Field of Search ............................... 435/69.1, 410, 435/419, 468; 800/278, 279, 295, 298, 301, 302

(56) References Cited

PUBLICATIONS

Zhang et al, "Activation of Salicyclic Acid–Induced Protein Kinase, a Mitogen–Activated Protein Kinase, Induces Multiple Defense Responses in Tobacco", Aug. 2001, The Plant Cell, vol. 13, pp. 1877–1889.*

Enyedi et al., "Localization, conjugation, and function of salicyclic acid in tobaco during the hypersensitive reaction to tobacco mosaic virus", Mar. 1992, Proc. Natl. Acad. Sci., vol. 89, pp. 2480–2484.*

Yu, "Elicitins from Phytophthora and basic resistance in tobacco", May 1995, Proc. Natl. Acad Sci., vol. 92, pp. 4088–4094.*

He et al, "Hypersensitive Response Elicited by Erwinia amylovora Harpin Requires Active Plant Metabolism", vol. 7, No. 2, pp. 289–291.*

Sanger et al, "Characteristics of a strong promoter fro figwort mosaic virus: comparison with the analogous 35S promoter from cauliflower mosaic virus and the regulated mannopine sysnthase promoter", 1990, Plant Molecular Biology vol. 14, pp. 433–443.*

Steve Whitham et al. The N gene tobacco confers resistance to tobacco mosaic virus in transgenic tomato, Proc. Natl. Sci. USA, vol. 93, pp. 8776–8781.*

Christiane Gatz et al., Regulation of a modified CaMV 35S promoter by the Tn10–encoded Tet repressor in transgenic tobacco Mol. Gen Genet (1991), 227, pp. 229–237.*

George N. Agrios, 15 plant diseases caused by nematodes, Plant Pathology, pp. 612–626.*

S. Seo, et al., "Tobacco MAP Kinase: A Possible Mediator in Wound Signal Transduction Pathways", Science, vol. 70, Dec. 22, 1995, pp. 1988–1992.

S. Zhang, et al., "The tobacco wounding–activated mitogen–activated protein kinase is encoded by SIPK", Proc. Natl. Acad. Sci. USA, vol. 95, pp. 7225–7230, Jun. 1998 Plant Biology.

S. Usami, et al., "Cutting activates a 46–kilodalton protein kinase in plants", Proc. Natl. Acad. Sci. USA, vol. 92, pp. 8660–8664, Sep. 1995 Biochemistry.

* cited by examiner

*Primary Examiner*—Ashwin Mehta
(74) *Attorney, Agent, or Firm*—Dann Dorfman Herrell & Skillman, P.C.

(57) ABSTRACT

Novel used for WIPK, a member of the mitogen-activated protein (MAP) kinase family, are provided, based on the discovery that the WIPK protein is activatable in association with development or enhancement of resistance to microbial pathogens. Thus, WIPK may play a critical role in signal transduction for activation of plant defenses against certain microbial pathogens. Methods are disclosed for making WIPK transgenic plants with enchanced resistance to disease causing agents. In addition, transgenic plants transformed with WIPK and having enhanced disease resistance are disclosed.

6 Claims, 8 Drawing Sheets

METHOD OF USING A PATHOGEN-ACTIVATABLE MAP KINASE TO ENHANCE DISEASE RESISTANCE IN PLANTS

This application is a §371 Application of PCT/US99/03882, filed Feb. 23, 1999 which in turn claims priority to U.S. Provisional Application No. 60/075,685, filed Feb. 24, 1998.

Pursuant to 35 U.S.C. §202(c), it is acknowledged that the U.S. Government has certain rights in the invention described herein, which was made in part with funds from the National Science Foundation, Grant numbers, MCB-9310371 and MCB-9723952.

FIELD OF THE INVENTION

This invention relates to the fields of molecular biology and genetic transformation in higher plants. More specifically, the invention relates to novel uses of genes and their encoded proteins that participate in a disease resistance pathway(s) in multicellular plants.

BACKGROUND OF THE INVENTION

Several publications are referenced in this application in parentheses in order to more fully describe the state of the art to which this invention pertains. Full citations for these references are found at the end of the specification. The disclosure of each of these publications is incorporated by reference herein.

Plant disease resistance is frequently associated with the formation of necrotic lesions, known as the hypersensitive response (HR), alterations in cell wall structure at the sites of infection, increases in endogenous salicylic acid (SA) levels, and activation of a complex array of defense-related genes, including the pathogenesis-related (PR) genes. In addition to these local responses, the uninfected portions of the plant usually develop systemic acquired resistance (SAR), which is manifested as enhanced resistance to a subsequent challenge by the initial or even unrelated pathogens. Activation of these defense responses is usually governed by a 'gene-for-gene' interaction between a plant resistance (R) gene and a pathogen avirulence (Avr) gene, or initiated by the plant recognition of non-race-specific elicitors such as elicitins.

Plant recognition of pathogens occurs either at the surface of plasma membrane or in the cytoplasm. Recent studies have revealed that various components in the plant defense signaling pathway(s) exhibit structural and functional conservation to those identified in animals. For example, several R gene products, including the N gene (which confers resistance to tobacco mosaic virus (TMV) in tobacco) share homology with the interleukin-1 receptor and Toll protein, both of which are involved in the induction of immune responses in mammals and Drosophila, respectively. In addition, a variety of signaling events, such as $Ca^{2+}$ flux, $H_2O_2$ burst generated by the activation of an NADPH oxidase, protein phosphorylation/dephosphorylation, and generation of oxylipin signaling molecules, have been associated with the induction of plant and animal defense responses.

Protein kinases and phosphatases have been implicated, through the use of their inhibitors, in the induction of several defense responses including medium alkalization, reactive oxygen species generation, defense gene activation and hypersensitive cell death. Kinase activities with characteristics of protein kinase C or MAP kinase have been associated with these processes. The MAP kinase cascade is one of the major pathways by which extracellular stimuli are transduced into intracellular responses in yeast and mammalian cells. In mammals, two of the three subfamilies of the MAP kinase family, the stress-activated protein kinase/Jun N-terminal kinase (SAPK/JNK) and the p38 kinase, are activated in response to various stress signals, including UV and ionizing radiation, hyperosmolarity, oxidative stress and cytokines.

A variety of MAP kinase genes have been isolated by PCR-based homology cloning from several plant species (Hirt, 1997; Mizoguchi et al., 1997). In addition, several kinase activities believed to be MAP kinases, based on the tact that they preferentially phosphorylate myelin basic protein (MBP) and are themselves phosphorylated on tyrosine residues upon activation, have been shown to be activated by stress stimuli. These include the tobacco wounding (cutting)-activated 46-kD kinase (Seo et al., 1995; Usami et al., 1995), the fungal elicitor-activated 47-kD kinase from tobacco (Suzuki & Shinshi, 1995), the harpin-activated 49-kD kinase from tobacco (Ádám et al., 1997), and the wounding-, systemin- and oligosaccharide-activated 48-kD kinase from tomato (Stratmann & Ryan, 1997).

Studies using an antibody against the C-terminal peptide of the alfalfa MMK4 have linked the alfalfa MMK4 to cold, drought and mechanical stresses (Jonak et al., 1996; Bögre et al., 1997). The same antibody was also used to demonstrate that parsley ERMK may encode the 45-kD MBP kinase activated by Pep25 elicitor derived from the *Phytophthora sojae* glycoprotein elicitor (Ligterink et al., 1997).

A 48-kD SA-induced protein kinase, termed SIPK, was identified in tobacco and its corresponding gene has been cloned using peptide sequences obtained by microsequencing of the purified protein (Zhang & Klessig, 1997; see also co-pending U.S. patent application Ser. No. 08/837,593, now U.S. Pat. No. 5,977,442, incorporated by reference herein). This MAP kinase was recently shown to be activated by various fungal elicitors (Zhang et al., 1998) and also by wounding (Zhang & Klessig, 1998) and by tobacco mosaic virus (TMV) infection (U.S. Ser. No. 08/837,593, now U.S. Pat. No. 5,977,442).

The aforementioned wounding-activated 46-kD protein kinase heretofore was believed to be encoded by WIPK, a member of tobacco MAP kinase family, since this gene is rapidly induced at the mRNA level by wounding (Seo et al., 1995). However, a rigorous demonstration of this has been lacking.

Genes that encode components of signal transduction pathways which are used by a plant to activate defense responses for protection against disease-causing agents can be used in a variety of ways to improve or enhance the disease resistance response in plants. Accordingly, a need exists to identify new genes that participate in such functions or, alternatively, to determine if certain genes that are already available also possess such functions.

SUMMARY OF THE INVENTION

In accordance with the present invention, it has now been discovered that the MAP kinase encoded by the tobacco WIPK gene is not activated by, and therefore not involved in, response to wounding, but rather is activatable in association with development or enhancement of resistance to microbial pathogens. Accordingly, the WIPK gene and its functional homologs in other species, and their encoded gene products, are useful for a variety of purposes relating to improving and enhancing a plant's disease resistance.

According to one aspect of the invention, a transgenic plant is provided, which exhibits enhanced resistance to plant disease-causing agents such as viruses (such as TMV), fungi (such as Phytophthora spp.), bacteria (such as Pseudomonas spp.) and nematodes. The transgenic plant is stably transformed with a DNA construct, expressible in the cell, encoding a WIPK enzyme. The WIPK coding sequence from tobacco is preferred for use in the DNA construct.

According to another aspect of the invention, a method of making a transgenic plant with enhanced disease resistance is provided. The method comprises (1) transforming regenerable cells of a plant with a recombinant DNA construct, expressible in a plant, encoding a WIPK enzyme; and (2) regenerating a transgenic plant from those transformed cells. For reasons described in greater detail below, such plants are expected to exhibit enhanced resistance to a variety of disease-causing agents, including viruses, bacteria, fungi and nematodes.

The novel functions of WIPK identified in accordance with this invention and described in greater detail below, indicate that WIPK may play a key role in signal transduction for activation of plant defenses against microbial pathogens or components thereof. Accordingly, the new methods, plant cells and plants of the invention offer a significant advance in the field of plant molecular biology, as it pertains to enhancing the plant disease resistance response.

BRIEF DESCRIPTION OF THE DRAWINGS

FIG. 1A: In-gel kinase activity assay. Extracts containing 15 µg protein were electrophoresed in 10% SDS-polyacrylamide gels imbedded with 0.25 mg/mL of MBP in the separating gel. After protein renaturation, the kinase reaction was carried out as described in Materials and Methods. The sizes of activated kinases are given in kilodaltons. FIG. 1B: The activities of 48-kD kinase (in TMV-[●] and mock-[○] inoculated leaves) and 44-kD kinase (in TMV-[▼] and mock-[△] inoculated leaves) were quantitated using a PhosphorImager and the relative activities were plotted against time. Kinase activities were normalized to the level present at the zero time point for the 48-kD kinase, which was given a value of 1.

FIG. 2A: An antibody raised against a peptide (p44N) corresponding to the unique N-terminus of WIPK, Ab-p44N, specifically recognized the WIPK protein. Two nanograms each of recombinant HisSIPK, HisNtf4, HisWIPK, and HisNtMPK6 or 20 µg of protein extracts from 48 hr mock- or TMV-inoculated tobacco leaves (maintained throughout infection at 22° C.) were subjected to immunoblot analysis with Ab-p44N in the absence or presence of 0.2 µg/mL competitor peptides p44N or p48N. FIG. 2B: Immuno-complex kinase assay of TMV-activated kinase using SIPK-specific antibody, Ab-p48N. Protein extracts (50 µg) from TMV- or mock-inoculated leaf tissue were reacted with Ab-p48N (2.5 µg). The resultant antigen-antibody complex were precipitated with protein A-agarose beads, washed extensively before addition to a kinase assay mixture with [γ-$^{32}$P]-ATP and MBP as substrates. The reaction mixture, including the phosphorylated MBP, were then fractionated by SDS-PAGE. FIG. 2C: Immuno-complex kinase assay of TMV-activated kinase using WIPK-specific antibody, Ab-p44N. Protein extracts (50 µg) from TMV- or mock-inoculated leaves were. immunoprecipitated with Ab-p44N (2.5 µg) and the kinase activity of the immuno-complex was determined as above. Times in B and C are given in hps from 32° C. to 22° C.

FIG. 3A: Increase in steady-state levels of WIPK mRNA in TMV-infected plants. Duplicates of leaf discs used in FIG. 1 were extracted for total RNA, thus facilitating direct comparison of the induction kinetics of mRNA and enzymatic activity. Twenty micrograms of total RNA per lane were separated on 1.2% formaldehyde-agarose gels and transferred to Zeta-probe membranes. Blots were hybridized with random primer-labeled inserts consisting of either a full-length cDNA of WIPK (data shown) or its 3'-untranslated region (data not shown). FIG. 3B: Increase of WIPK protein in TMV-infected tobacco after temperature shift. Samples containing 20 µg of protein from the leaf extracts used for FIG. 1A were separated on 10% SDS-polyacrylamide gels. After blotting to nitrocellulose, the WIPK protein was detected with Ab-p44N.

FIGS. 4A–4C. Activation of WIPK by TMV in tobacco plants (cv Xanthi nc [NN]) maintained at 22° C. throughout infection. FIG. 4A: Increase in steady-state levels of WIPK mRNA in TMV-infected tobacco plants. Tobacco plants were inoculated with TMV or buffer (mock) as in FIG. 1 except a higher concentration of TMV was used (5 µg/mL). Leaf discs were taken at the indicated times in hr post inoculation (hpi). Total RNA was prepared and analyzed for WIPK mRNA as described in FIG. 3. FIG. 4B: Increase of WIPK protein in TMV-infected tobacco maintained at 22° C. Protein extracts were prepared from duplicate leaf discs to those used in FIG. 4A. Twenty micrograms of protein was analyzed by immunoblotting using Ab-p44N as described in FIG. 3. FIG. 4C: Induction of WIPK enzymatic activity in TMV-infected tobacco maintained at 22° C. Selected protein extracts from (B) were analyzed by immuno-complex kinase assay using WIPK-specific Ab-p44N as described in FIG. 2.

FIG. 6A: WIPK mRNA induction in tobacco by TMV infection is N gene dependent. TMV-susceptible tobacco plants (*N. tabacum* cv Xanthi [nn] which lacks N resistance gene) were infected and WIPK mRNA detected by RNA gel blot analysis. FIG. 6B: Induction of WIPK mRNA by TMV infection is SA independent. Transgenic tobacco (cv Xanthi nc [NN]) plants expressing the NahG gene were infected and WIPK mRNA determined by RNA gel blot analysis. FIG.

6C: Systemic induction of WIPK mRNA after TMV infection. Three leaves from each tobacco plants (cv Xanthi nc [NN]) were either inoculated with TMV or buffer only (mock) and maintained at 22° C. At indicated days post inoculation (dpi), leaf discs were taken from the upper uninoculated leaves. Total RNA was isolated and WIPK mRNA levels were determined.

Figure 7A:
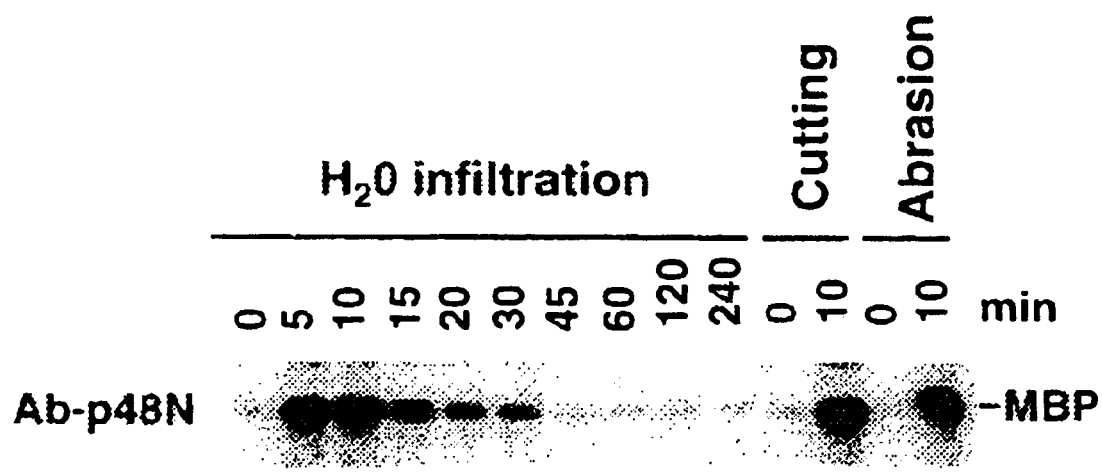
Figure 7B:
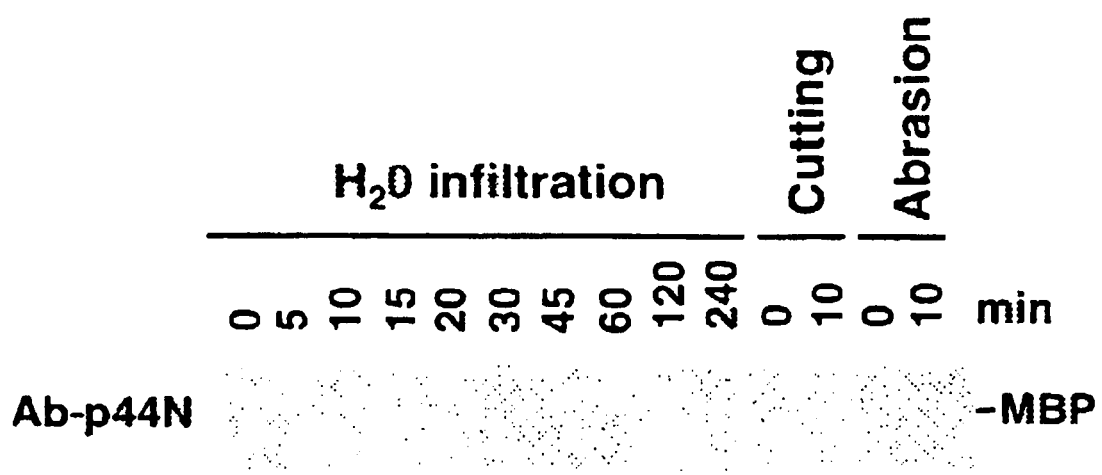

FIGS. 7A and 7B. Autoradiograms of immunoblot assays showing that the 48-kD MBP kinase activated by water infiltration and wounding is encoded by SIPK rather than WIPK. Protein extracts (50 μg) from water-infiltrated, cutting or abrasion-wounded leaves were immunoprecipitated with either the SIPK-specific antibody Ab-p48N (FIG. 7A) or the WIPK-specific antibody Ab-p44N (FIG. 7B). Kinase activity of the resultant immuno-complexes was subsequently determined as described in Example 1.

Figure 8A:
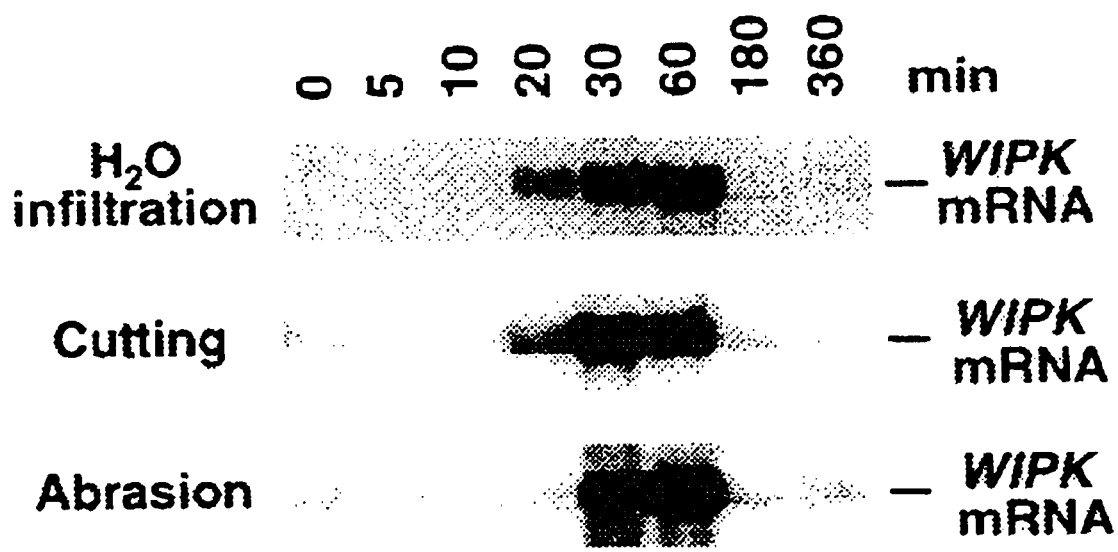
Figure 8B:
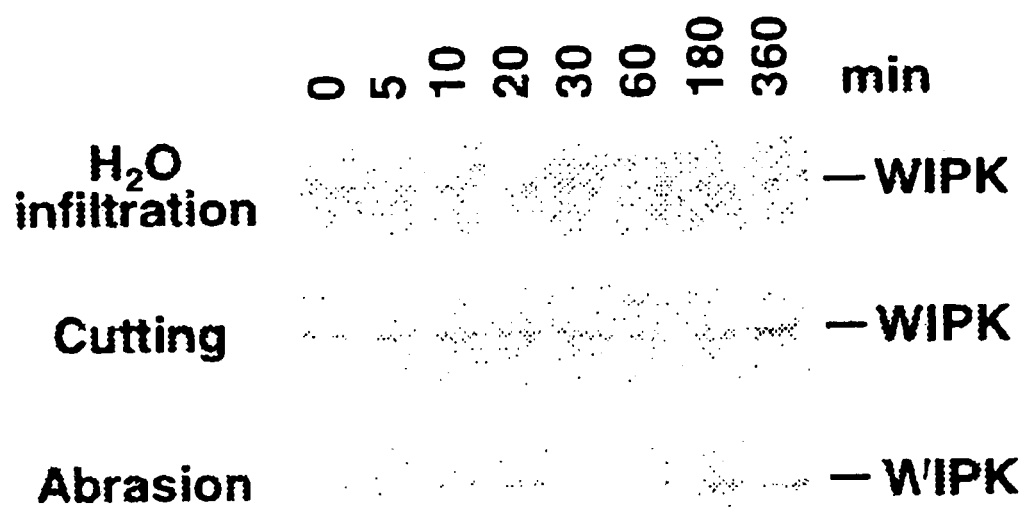

FIGS. 8A and 8B. Autoradiograms of RNA or immunoblot assays showing that water infiltration and wounding induce transient increases in WIPK mRNA levels, but little or no increases in WIPK protein level. FIG. 8A: Total RNA was extracted at the indicated times from water infiltrated or wounded leaves and subjected to RNA gel blot analysis. Blots were sequentially hybridized with the 3' UTR and then the full length WIPK cDNA. Both probes yielded the same result; thus, only the autoradiogram produced with the full-length cDNA is shown. FIG. 8B: Protein extracts (20 μg) were subjected to immunoblot analysis with the WIPK-specific antibody, Ab-p44N.

DETAILED DESCRIPTION OF THE INVENTION

I. Definitions

Various terms relating to the present invention are used hereinabove and also throughout the specifications and claims.

The term "substantially pure" refers to a preparation comprising at least 50–60% by weight the compound of interest (e.g., protein, nucleic acid, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

With respect to proteins, the term "isolated protein" or "isolated and purified protein" is sometimes used herein. This term may refer to a protein which has been sufficiently separated from other proteins with which it would naturally be associated, so as to exist in substantially pure form (as defined above). This term may also refer to a protein produced by expression of an isolated nucleic acid molecule encoding the protein.

With reference to nucleic acids, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a substantially pure form (as defined above).

With respect to antibodies, the term "immunologically specific" refers to antibodies that bind to one or more epitopes of a protein of interest, but which do not substantially recognize and bind other molecules in a sample containing a mixed population of antigenic biological molecules.

The term "specifically hybridizing" refers to the association between two single-stranded nucleotide molecules of sufficiently complementary sequence to permit such hybridization under pre-determined conditions generally used in the art (sometimes termed "substantially complementary"), to the substantial exclusion of hybridization with single-stranded nucleic acids of non-complementary sequence.

The term "pathogen-inoculated" refers to the inoculation of a plant with a pathogen.

The term "disease defense response" or "disease resistance response" refers to a change in metabolism, biosynthetic activity or gene expression that enhances the plant's ability to suppress the replication and spread of a microbial pathogen (i.e., to resist the microbial pathogen). Examples of plant disease defense responses include, but are not limited to, production of low molecular weight compounds with antimicrobial activity (referred to as phytoalexins) and induction of expression of defense (or defense-related) genes, whose products include, for example, peroxidases, cell wall proteins, proteinase inhibitors, hydrolytic enzymes, pathogenesis-related (PR) proteins and phytoalexin biosynthetic enzymes, such as phenylalanine ammonia lyase and chalcone synthase. Such defense responses appear to be induced in plants by several signal transduction pathways involving secondary defense signaling molecules produced in plants. Certain of these defense response pathways are SA dependent, while others are partially SA dependent and still others are SA independent. Agents that induce disease defense responses in plants include, but are not limited to: (1) microbial pathogens, such as fungi, bacteria, viruses and nematodes; (2) microbial components and other defense response elicitors, such as proteins and protein fragments, small peptides, β-glucans, elicitins (a family of small extracellular proteins produced by the pathogenic fungal genus Phytophthora), harpins (a bacterial-encoded elicitor) and oligosaccharides; and (3) secondary defense signaling molecules produced by the plant, such as SA, $H_2O_2$, ethylene and jasmonates.

The terms "defense-related genes" and "defense-related proteins" refer to genes or their encoded proteins whose expression, synthesis or activation is associated with (induced or activated after) infection with a pathogen to which the plant is usually resistant.

The term "wounding response" refers to a change in metabolism, biosynthetic activity or gene expression that occurs in a plant in response to wounding (e.g., cutting, abrasion).

The term "wounding-related genes" and "wounding-related proteins" refer to genes or their encoded proteins whose expression, synthesis or activation is associated with (induced or activated after) wounding of a plant. These genes are also sometimes referred to as "wounding inducible" genes. Wounding inducible genes also may be defense related genes (i.e. they may be induced in a disease defense response or a wounding response, with similar or differing kinetics of induction).

The term "promoter region" refers to the 5' regulatory regions of a gene (e.g., CaMV 35S promoters and/or tetracycline repressor/operator gene promoters).

The term "reporter gene" refers to a nucleic acid coding sequence that encodes a readily detectable gene product, which may be operably linked to a promoter region to form a chimeric gene, such that expression of the coding sequence is regulated by the promoter and the product of the coding sequence is readily assayed.

The term "selectable marker gene" refers to a gene that when expressed confers a selectable phenotype, such as antibiotic resistance, on a transformed cell or plant.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The term "DNA construct" refers to genetic sequence used to transform plant cells and generate progeny transgenic plants. At minimum a DNA construct comprises a coding region for a selected gene product, operably linked to 5' and 3' regulatory sequences for expression in transformed plants. In preferred embodiments, such constructs are chimeric, i.e., the coding sequence is from a different source one or more of the regulatory sequences (e.g., coding sequence from tobacco and promoter from cauliflower mosaic virus). However, non-chimeric DNA constructs also can be used. DNA constructs may be administered to plants in a viral or plasmid vector. Other methods of delivery such as Agrobacterium T-DNA mediated transformation and transformation using the biolistic process are also contemplated to be within the scope of the present invention. The transforming DNA may be prepared according to standard protocols such as those set forth in Ausubel et al. (1997). A plant species or cultivar may be transformed with a DNA construct (chimeric or non-chimeric) that encodes a polypeptide from a different plant species or cultivar (e.g., tobacco transformed with a gene encoding an Arabidopsis protein). Alternatively, a plant species or cultivar may be transformed with a DNA construct (chimeric or non-chimeric) that encodes a polypeptide from the same plant species or cultivar.

II. Description of the Invention

The WIPK gene was initially cloned from tobacco (Seo et al., 1995) and purported to be involved in intracellular signaling in response to wounding. It has now been discovered in accordance with the present invention that WIPK, though induced at the mRNA level by wounding as originally reported, is not involved in wounding responses. Instead, the WIPK protein is activated by pathogen infection or by treatment with certain pathogen-derived elicitors, such as eliciting.

In Example 1, we show that TMV infection activates a 44-kD kinase in tobacco plants carrying the N resistance gene. By using a WIPK-specific antibody (e.g., Ab-p44N), this 44-kD kinase was shown to be encoded by WIPK. In contrast to SIPK from tobacco and MAP kinases from yeast and mammals, activation of WIPK is preceded by a rise in mRNA levels and de novo synthesis of WIPK protein. Based on the discovery that WIPK gene activation is N gene dependent, systemic, and salicylic acid (SA) independent, we believe that WIPK is an important signaling component upstream of SA in both local and systemic defense responses of tobacco against TMV, or alternatively, WIPK is part of a SA-independent pathway leading to disease resistance. Using the WIPK-specific antibody, we also show in Example 1 that, while WIPK mRNA increases as a result of wounding, there is little or no increase in the level of WIPK protein in response to wounding and little or no WIPK-encoded kinase activity. In addition to the experimental results described in Example 1, it has been determined that WIPK is activated by exposure to harpin, a bacterial-encoded elicitor, and to the fungal eliciting, parasiticein and cryptogein.

Based on the aforementioned discovery of novel is functions for WIPK, the present invention is drawn to methods of using the WIPK gene or its functional homologs from other species to enhance the disease defense response in transgenic plants containing the gene. The following description sets forth the general procedures involved in practicing the present invention. To the extent that specific materials are mentioned, it is merely for purposes of illustration and is not intended to limit the invention. Unless otherwise specified, general cloning procedures, such as those set forth in Sambrook et al., (1989) or Ausubel et al. (1997) are used.

A. Preparation of WIPK and WIPK Homologs

A tobacco WIPK cDNA has been isolated and its deduced amino acid sequence reported (Seo et al., 1995). Although use of such a tobacco WIPK cDNA is exemplified herein, this invention is intended to encompass the use of WIPK nucleic acids and WIPK proteins from other plant species that are sufficiently similar to be used instead of the tobacco WIPK nucleic acid and proteins for the purposes described below. These include, but are not limited to, allelic variants and natural mutants of tobacco WIPK, which are likely to be found in any given tobacco cultivar. These also include functional homologs from other plant species within the confines of homology set forth below.

Because inter-cultivar and inter-species variants are expected to possess certain differences in nucleotide and amino acid sequence, this invention contemplates use of a WIPK nucleic acid molecule that encodes a WIPK polypeptide having at least about 70%, preferably about 80% and most preferably about 90% identity with the tobacco WIPK deduced amino acid sequence reported by Seo et al. (1995). Because of the natural sequence variation likely to exist among WIPK genes and their encoded proteins, one skilled in the art would expect to find such sequence variation, while still maintaining the unique properties of the WIPK gene and encoded polypeptides intended for use in the present invention. Such an expectation is due in part to the degeneracy of the genetic code, as well as to the known evolutionary success of conservative amino acid sequence variations, which do not appreciably alter the nature of the encoded protein. Accordingly, such variants are considered substantially the same as one another and are included within the scope of the present invention.

For purposes of this invention, the term "substantially the same" refers to nucleic acid or amino acid sequences having sequence variation that do not materially affect the nature of the protein (i.e. its structure and/or biological activity). With particular reference to nucleic acid sequences, the term "substantially the same" is intended to refer to coding regions and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide that do not affect structure or function. The terms "percent identity" and "percent similarity" are also used herein in comparisons among amino acid sequences. These terms are intended to be defined as they are in the UWGCG sequence analysis program (Devereaux et al., 1984), available from the University of Wisconsin.

WIPK nucleic acid molecules of the invention may be prepared by two general methods: (1) they may be synthesized from appropriate nucleotide triphosphates, or (2) they may be isolated from biological sources. Both methods utilize protocols well known in the art.

The availability of nucleotide sequence information, such as the cDNA sequence of tobacco WIPK, enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides must be synthesized in stages, due to the size limitations inherent in current oligonucleotide synthetic methods. Thus, for example, a long double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct a full-length double-stranded molecule. A synthetic DNA molecule so constructed may then be cloned and amplified in an appropriate vector.

WIPK genes or cDNAs also may be isolated from appropriate biological sources using methods known in the art. For instance, the tobacco WIPK has been isolated by the present inventors and by others. Homologs of the tobacco WIPK DNA may be identified by using hybridization and washing conditions of appropriate stringency. For example, hybridizations may be performed, according to the method of Sambrook et al. (1989), using a hybridization solution comprising: 5×SSC, 5× Denhardt's reagent, 1.0% SDS, 100 µg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 2×SSC and 0.1% SDS; (4) 2 hours at 45–55° in 2×SSC and 0.1% SDS, changing the solution every 30 minutes.

Nucleic acids to be used in the present invention may be maintained as DNA in any convenient cloning vector. In a preferred embodiment, clones are maintained in plasmid cloning/expression vector, such as pGEM (Promega Biotech, Madison, Wis.) or pBluescript (Stratagene, La Jolla, Calif.), either of which is propagated in a suitable *E. coli* host cell. WIPK nucleic acid molecules contemplated for use in the present invention include cDNA, genomic DNA, RNA, and fragments thereof which may be single- or double-stranded.

The availability of nucleic acid molecules encoding WIPK enables production of the proteins using in vitro expression methods known in the art. For example, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md.

According to a preferred embodiment, larger quantities of WIPK polypeptides may be produced by expression in a suitable procaryotic or eucaryotic system. For example, part or all of a WIPK DNA molecule may be inserted into a plasmid vector adapted for expression in a bacterial cell (such as *E. coli*) or a yeast cell (such as *Saccharomyces cerevisiae*), or into a baculovirus vector for expression in an insect cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The WIPK polypeptide produced by gene expression in a recombinant procaryotic or eucyarotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein (e.g., Ab p44N, prepared by the present inventors), or by metal-chelate affinity chromatography (e.g., for purification of histidine-tailed fusion proteins). Such methods are commonly used by skilled practitioners. WIPK protein produced by any of the above-described methods can be used, for instance, as a research tool to study the interaction of WIPK with upstream (e.g. WIPK kinase) or downstream components of the WIPK-mediated signal transduction pathway.

B. Methods of Using WIPK and WIPK Homologs

Since WIPK or its homologs are likely involved in a MAP kinase signal transduction cascade that activates defense gene expression, transgenic plants with altered WIPK expression are expected to exhibit altered activation of multiple plant disease defense genes, such as PR genes. These plants should be superior with respect to protection against microbial pathogens, as compared with non-transgenic plants that express only one or two plant defense genes. Moreover, induction of disease resistance in WIPK transgenic plants is expected to be inheritable, and should not require use of chemical inducers, such as SA or its synthetic counterparts, INA or BTH, for the activation of the disease defense response. Thus, these transgenics should provide an economically and environmentally sound alternative to the use of chemical pesticides, which can be costly and environmentally damaging.

Without intending to limit the invention in any way, the inventors offer the following discussion of the mechanisms by which WIPK transgenic plants are expected to exhibit enhanced resistance to microbial pathogens. WIPK, like all MAP kinases, is activated post-translationally by phosphorylation by the upstream MAP kinase kinase (in this instance WIPK kinase). Thus, in wild type plants, after an appropriate signal (e.g., TMV infection) is perceived, the WIPK gene first must be transcribed and translated before the protein can be activated. As a result, there is a delay between the signal event and the appearance of WIPK activity.

For the foregoing reason, simply constitutively expressing, or overexpressing, the WIPK gene at the mRNA and protein levels will not necessarily stimulate the defense pathway in which WIPK is a critical component. Instead, constitutive or inducible overexpression of a WIPK transgene may result in a larger pool of WIPK in the plant, which then can be rapdily activated by the appropriate trigger. Having a large pool of inactive, but activatable WIPK (as opposed to constitutively active WIPK) could be advantageous for the transgenic plant, bearing in mind that WIPK activation has been observed by the inventors to be associated with cell death. If activated WIPK leads to localized cell death (which is a known disease defense response in plants), then plants having a increased pool of WIPK mRNA and/or WIPK protein will be primed to rapidly respond to the activation signal (e.g., invasion by a pathogenic microorganism).

On the other hand, if a constitutively activated WIPK pathway is not deleterious to the plant, but instead is advantageous, then WIPK can be used to advantage to isolate upstream components of the signal transduction pathway, one purpose of which would be to make those components constitutively active as well (this use of WIPK is described in greater detail below). Thus, transgenic plants expressing a constitutively active mutant WIPK kinase could exhibit a constitutively active WIPK pathway, thereby enhancing the plant's resistance to microbial pathogens on an ongoing basis.

Transgenic plants expressing the WIPK gene can be generated using standard plant transformation methods known to those skilled in the art. These include, but are not limited to, Agrobacterium vectors, PEG treatment of protoplasts, biolistic DNA delivery, UV laser microbeam, gemini virus vectors, calcium phosphate treatment of protoplasts, electroporation of isolated protoplasts, agitation of cell suspensions with microbeads coated with the transforming DNA, direct DNA uptake, liposome-mediated DNA uptake, and the like. Such methods have been published in the art. See, e.g., *Methods for Plant Molecular Biology* (Weissbach & Weissbach, eds., 1988); *Methods in Plant Molecular Biology* (Schuler & Zielinski, eds., 1989); *Plant Molecular Biology Manual* (Gelvin, Schilperoort, Verma, eds., 1993); and *Methods in Plant Molecular Biology—A Laboratory Manual* (Maliga, Klessig, Cashmore, Cruissem & Varner, eds., 1994).

The method of transformation depends upon the plant to be transformed. The biolistic DNA delivery method is useful for nuclear transformation. In another embodiment of the invention, Agrobacterium vectors are used to advantage for efficient transformation of plant nuclei.

In a preferred embodiment, the gene is introduced into plant nuclei in Agrobacterium binary vectors. Such vectors include, but are not limited to, BIN19 (Bevan, 1984) and derivatives thereof, the pBI vector series (Jefferson et al., 1987), and binary vectors pGA482 and pGA492 (An, 1986).

The WIPK gene may be placed under a powerful constitutive promoter, such as the Cauliflower Mosaic Virus (CaMV) 35S promoter or the figwort mosaic virus 35S promoter. Transgenic plants expressing the WIPK gene under an inducible promoter are also contemplated to be within the scope of the present invention. Inducible plant promoters include the tetracycline repressor/operator controlled promoter.

Using an Agrobacterium binary vector system for transformation, the WIPK coding region, under control of a constitutive or inducible promoter as described above, is linked to a nuclear drug resistance marker, such as kanamycin resistance. Agrobacterium-mediated transformation of plant nuclei is accomplished according to the following procedure:

(1) the gene is inserted into the selected Agrobacterium binary vector;
(2) transformation is accomplished by co-cultivation of plant tissue (e.g., leaf discs) with a suspension of recombinant Agrobacterium, followed by incubation (e.g., two days) on growth medium in the absence of the drug used as the selective medium (see, e.g., Horsch et al. 1985);
(3) plant tissue is then transferred onto the selective medium to identify transformed tissue; and
(4) identified transformants are regenerated to intact plants.

It should be recognized that the amount of expression, as well as the tissue specificity of expression of the WIPK gene in transformed plants can vary depending on the position of their insertion into the nuclear genome. Such position effects are well known in the art. For this reason, several nuclear transformants should be regenerated and tested for expression of the transgene.

In some instances, such as in the study of the WIPK-mediated signal transduction pathway, it may be desirable to down-regulate or inhibit expression of endogenous WIPK in plants possessing the gene. Accordingly, WIPK nucleic acid molecules, or fragments thereof, may also be utilized to control the production of WIPK, thereby regulating the amount of protein available to participate in disease resistance signalling pathways. Alterations in the physiological amount of WIPK may act synergistically with other agents used to protect plants during pathogen attack. In one embodiment, full-length WIPK antisense molecules or antisense oligonucleotides, targeted to specific regions of WIPK-encoded RNA that are critical for translation, are used. The use of antisense molecules to decrease expression levels of a pre-determined gene is known in the art. In a preferred embodiment, antisense molecules are provided in situ by transforming plant cells with a DNA construct which, upon transcription, produces the antisense sequences. Such constructs can be designed to produce full-length or partial antisense sequences.

In another embodiment, overexpression of WIPK is induced to generate a co-suppression effect. This excess expression serves to promote down-regulation of both endogenous and exogenous WIPK genes.

Optionally, transgenic plants can be created containing mutations in the region encoding the active site of WIPK. This embodiment is preferred over the use of anti-sense constructs due to the very high homology between MAP kinases. For example, a mutated WIPK could be made in which the encoded kinase is permanently inactive but unaltered in its binding to upstream signalling components, such as MAP kinase kinases. This mutant protein could still serve as the substrate for upstream MAP signalling molecules and physically compete with the wild-type WIPK, but would not transduce signal to downstream components. Thus, it may be possible to specifically block the pathway without affecting other MAP kinase cascades.

WIPK can also be used as "bait" to clone the upstream WIPK kinase by a yeast two-hybrid system (see Ausubel et al., 1997 for standard protocols). The identity of WIPK kinase should be evident from the DNA sequence, since MAPK kinases are highly conserved among organisms, including plants (Mizoguchi et al., 1996). If the WIPK kinase is not identified on an initial screen, use of a mutant form of WIPK as bait in a two-hybrid screen may increase the probability of identifying WIPK kinase. By changing the TEY phosphorylation site to EEE or AEA, the stability of the interaction between WIPK and its kinase may be increased; phosphorylation has been shown to weaken the interaction between a kinase and its substrate for the mammalian Erk2 kinase and Mnk1 and the Drosophila p38 kinase kinase and p38 kinase, respectively. A putative WIPK kinase isolated through this process would then be tested for its ability to phosphorylate WIPK in vitro. To do this, His- or GST-tagged recombinant WIPK kinase can be activated by incubation with an extract from elicitin-treated cells, then purified on a nickel or glutathione matrix and incubated with recombinant WIPK and [γ-$^{32}$P]ATP. Another way to demonstrate that the cloned MAPK kinase is WIPK kinase is to prepare antibodies against a unique region of the putative WIPK kinase, based on sequence comparisons with other plant, animal and yeast MAPK kinases. These antibodies can then be used to immunoprecipitate WIPK kinases from extracts prepared from radiolabeled untreated or elicitin-treated tobacco cells. Since WIPK kinase is itself activated via phosphorylation by the upstream WIPK kinase kinase, the authentic WIPK kinase should exhibit an increase in phosphorylation following elicitin treatment. In addition, the in vivo activated putative WIPK kinase may retain its activity during immunoprecipitation and, therefore, be capable of phosphorylating the recombinant WIPK in vitro, thereby establishing its identity. It may also be possible to determine the specificity of the putative WIPK kinase for WIPK in vivo, by co-transfection in tobacco protoplasts of the WIPK kinase gene together with different MAPK genes.

Another approach to cloning WIPK kinase is to use recombinant WIPK as a substrate for the biochemical purification of activated WIPK kinase from elicitin-treated tobacco suspension cells, analogous to the method by which SIPK was purified using MBP as the substrate (Zhang & Klessig, 1997). To ensure that the kinase phosphorylating WIPK is WIPK kinase, rather than another kinase, WIPK activation, as well as phosphorylation, would be monitored. In addition, this WIPK phosphorylating activity should be much higher in elicitin-treated cells, as compared with untreated cells. Once purified, its partial amino acid sequence can be utilized to create degenerate oligonucleotides, which can then be used to isolate the encoding gene from a tobacco cDNA library.

Once cloned, a constitutively activated WIPK kinase may be constructed, as has been done for mammalian (Mansour et al., 1994) and Xenopus (Gotoh et al., 1994) MAPK kinases. MAPK kinases are activated by dual phosphorylation of a SXXXS/T motif (SEQ ID NO: 1) in the kinase subdomain VIII by MAPK kinase kinase. Substitution of these two Ser/Thr residues with Asp or Glu was found to increase basal activity about 100 fold, and cells transformed with these mutants exhibited constitutive activation of the MAPK regulated pathway (i.e. AP-1 transcription; Mansour et al., 1994). The constitutively activated mutatn WIPK will be transformed into plant cells and the corresponding transgenic plants obtained. These plants will have the WIPK-mediated signal transduction pathway constitutively activated.

From the foregoing discussion, it can be seen that WIPK and its homologs, and transgenic plants containing them will be useful for the regulation of the disease resistance pathway in plants and for enhancing resistance to plant pathogens. This provides an economically and ecologically viable alternative to the use of chemical agents to control plant disease.

The following example is intended to illustrate embodiments of the invention. It is not intended to limit the scope of the invention in any way.

EXAMPLE 1

The experimental methods set forth below were used to discover and characterize the novel features of WIPK described in accordance with the present invention. Those features are discussed in detail in this example.

Materials and Methods

Treatment of tobacco. Tobacco plants (*N. tabacum* cv Xanthi nc[NN]; *N. tabacum* cv Xanthi [nn]; and *N. tabacum* cv Xanthi nc[NN]/NahG transgenic) were grown at 22° C. in a growth room programmed for a 14-hr light cycle.

For TMV inoculations, seven to eight week old tobacco plants were either inoculated with TMV (U1 strain, 1 $\mu$g/mL or as indicated in 50 mM phosphate buffer, pH 7.0) or buffer only (mock). After infection, plants were either maintained at 32° C. for 48 hr before transferred to 22° C. for temperature shift experiment or maintained at 22° C. throughout the infection in a growth chamber. Discs from the infected leaves were collected at various time, quickly frozen in liquid nitrogen and stored at −80° C. until analysis.

For water treatment, one leaf from each plant was injected with solution using a syringe until the entire leaf was infiltrated. At various times, leaf discs were collected and treated as described above.

Wounding experiments were performed according to Usami et al., 1995 and Seo et al., 1995.

Preparation of protein extracts. Leaf discs (4 discs, each −1 cm in diameter) were first ground to a fine powder in 1.5 mL microcentrifuge tubes using small plastic pestles. After adding 0.25 mL extraction buffer (100 mM HEPES, pH 7.5, 5 mM EDTA, 5 mM EGTA, 10 mM DTT, 10 mM $Na_3VO_4$, 10 mM NaF, 50 mM b-glycerolphosphate, 1 mM phenylmethylsulfonyl fluoride, 5 $\mu$g/mL antipain, 5 $\mu$g/mL aprotinin, 5 $\mu$g/mL leupeptin, 10% glycerol, 7.5% polyvinylpolypyrrolidone), the mixture was sonicated for 15 seconds with a W-375 Sonicator (Heat System-Ultrasonics, Inc., NY) fitted with a microprobe at setting 4 and 80% duty cycle. After centrifugation at 13,000 rpm for 30 min in a microfuge, supernatants were transferred into clean tubes, quickly frozen in liquid nitrogen and stored at −80° C.

The concentration of protein extracts was determined using the Bio-Rad protein assay kit (Bio-Rad, CA) with BSA as standard.

In-gel kinase activity assay. The in-gel kinase activity assay was performed as described previously (zhang & Klessig, 1997). The relative kinase activity were quantitated using a PhosphorImager (Molecular Dynamics Inc., Sunnyvale, Calif.) and normalized to the level present at the zero time point for the 48-kD kinase, which was given a value of 1.

Antibody production and immunoblot analysis. The peptides p44N (MADANMGAGGGQFPDFPS; SEQ ID NO: 2) and p48N (MDGSGQQTDTMMSDAGAEQPPTAP; SEQ ID NO: 3), which correspond respectively to the unique N-termini of the WIPK and the SIPK proteins, were synthesized and conjugated to keyhole limpet hemacyanin (KLH) carrier. Polyclonal antisera were raised in rabbits and purified by affinity column chromatography (Zymed Laboratory, South San Francisco, Calif.).

For immunoblot analysis, 20 $\mu$g of total protein per lane were separated on 10% SDS-polyacrylamide gels, and the proteins were transferred to nitrocellulose membranes (Schleicher & Schuell, Inc., Keene, N.H.) by semi-dry electroblotting. After blocking for 1 hr in TBS buffer (20 mM Tris, pH 7.5, 150 mM NaCl, 0.1% Tween 20) with 5% nonfat dried milk (Carnation) at room temperature, the membranes were incubated with either Ab-p48N (raised against a peptide corresponding to the N-terminal 24 amino acids which are unique to SIPK (Zhang & Klessig, 1997, Zhang et al., 1998) or Ab-p44N antibody (0.5 µg/mL final concentration in TBS buffer) for 1 hr (Zhang et al., 1998). Following washing in TBS buffer for 4 times, the blots were incubated with a horseradish peroxidase-conjugated secondary antibody (Sigma, 1:10,000 dilution), and the complexes visualized using an enhanced chemiluminescence kit (DuPont) following the manufacturer's instructions.

Immuno-complex kinase activity assay. For immuno-complex kinase activity assay, protein extract (50 µg) was incubated with either Ab-p48N (2.5 µg) or Ab-p44N (2.5 µg) in immunoprecipitation buffer (20 mM Tris, pH 7.5, 150 mM NaCl, 1 mM EDTA, 1 mM EGTA, 1 mM $Na_3VO_4$, 1 mM NaF, 10 mM b-glycerolphosphate, 2 µg/mL antipain, 2 µg/mL aprotinin, 2 µg/mL leupeptin, 0.1% Tween 20) at 4° C. for 2 hr on a rocker. About 20 mL packed volume of protein A-agarose washed in immunoprecipitation buffer was added, and the incubation was continued for another 4 hr. Agarose bead-protein complexes were pelleted by brief centrifugation and washed three times with 1.5 mL immunoprecipitation buffer, once with immunoprecipitation buffer plus 1 M NaCl, and then three times with 1 mL kinase reaction buffer. Kinase activity in the complex (equivalent to 20 µg of starting protein) was assayed at room temperature for 20 min in a final volume of 25 µL containing 0.1 mg/mL of MBP, 10 µM of ATP with 1 µCi of [g-$^{32}$P]-ATP. The reaction was stopped by the addition of SDS-PAGE sample loading buffer. After electrophoresis on a 15% SDS-polyacrylamide gel, the phosphorylated MBP was visualized by autoradiography.

RNA gel blot analysis. RNA was extracted using Trizol reagent (Gibco BRL, Gaithersburg, Md.) following the manufacturer's instructions. Twenty micrograms of total RNA per lane were separated on 1.2% formaldehyde-agarose gels and transferred to Zeta-probe membranes (Bio-Rad). Blots were hybridized with random primer-labeled inserts consisting of either a full-length or an untranslated region (5'- and 3'-UTR for SIPK and WIPK, respectively) of SIPK or WIPK cDNA as previously described (Zhang et al., 1998).

Treatment of protein extracts with phosphatases. Protein extracts were prepared in the absence of phosphatase inhibitors from TMV-infected leaves at 8 hr after shifting plants from 32° C. to 22° C. or 48 hr after infection at 22° C. Samples containing 20 µg of protein were treated with either the serine/threonine-specific phosphatase, PP-$2A_1$ (0.25 units in 30 µL; Upstate Biotechnology, Lake Placid, N.Y.), or the tyrosine-specific protein phosphatase, YOP (2 units in 30 µL; NEB), for 20 min at 30° C. in the presence or absence of a phosphatase inhibitor. The PP-$2A_1$ inhibitor, okadaic acid, and YOP inhibitor, $Na_3VO_4$ were used at a concentration of 1 µM and 1 mM, respectively. After phosphatase treatment, kinase activity was detected by the in-gel kinase activity assay.

Results

TMV infection activates the 48-kD SIPK along with a 44-kD kinase in tobacco. Previously, we reported the activation of the 48-kD SIPK by SA, TMV, various fungal elicitors and wounding. Here, we describe our studies to determine whether infection by the viral pathogen TMV also activates other kinases in the resistant Xanthi nc (NN) tobacco. To more readily follow changes in kinase activity, advantage was taken of the reversible, high temperature inhibition of TMV-induced defense responses in these plants. At 32° C., TMV-infected tobacco fail to (i) produce elevated levels of SA, (ii) synthesize PR proteins, (iii) restrict virus multiplication and spread, and (iv) develop necrotic lesions. Upon shifting these plants to lower temperatures (22° C.), all of the above defense responses are rapidly and strongly induced in a more synchronous manner.

Figure 1A:
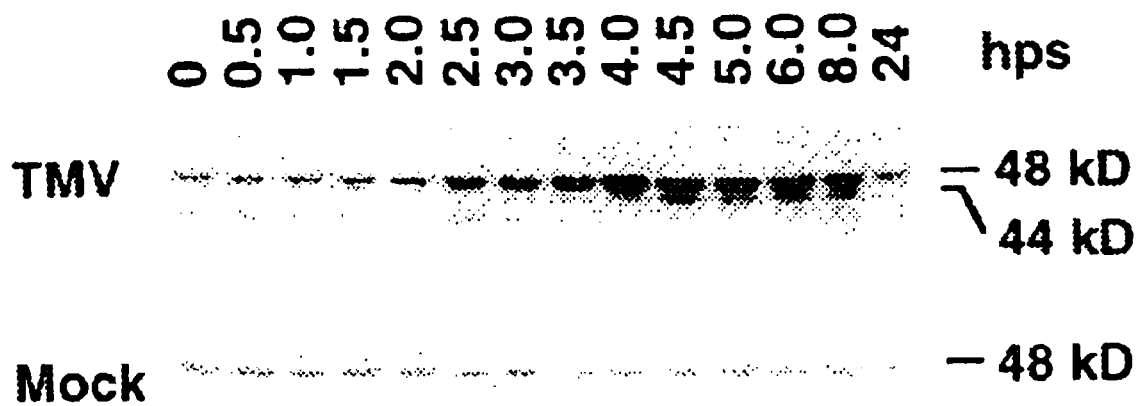
FIGS. 1A and 1B. Activation of 48-kD and 44-kD kinases in TMV-infected tobacco. Tobacco plants carrying N resistance gene (*N. tabacum* cv Xanthi nc [NN]) were inoculated with either TMV (U1 strain, 1 µg/mL in 50 mM phosphate buffer, pH 7.0) or buffer only (mock). After infection, plants were maintained at 32° C. for 48 hr. Discs from the infected leaves were collected at various time after the plants were shifted back to 22° C. (hps, hr post shift) and protein extracts were prepared.
Figure 1B:
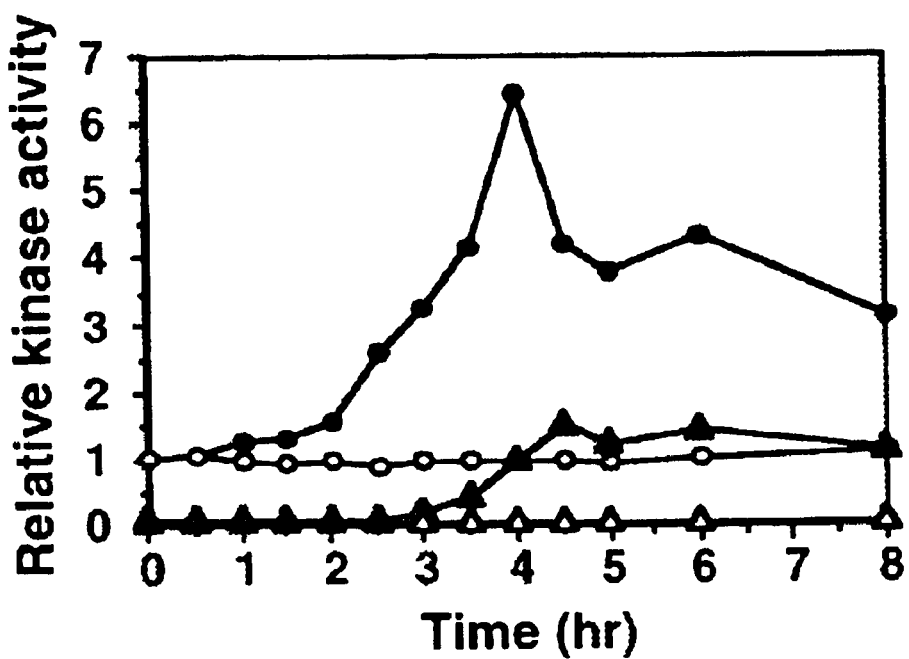

Using an in-gel kinase activity assay with MBP as the substrate, we observed that a 48-kD kinase and a 44-kD kinase were activated within 4 hr post shifting (hps) TMV-, but not mock-, infected plants to 22° C. (FIG. 1). The size and substrate preference of the 48-kD kinase were consistent with those of the previously identified SIPK. Moreover, this 48-kD protein was recognized by the SIPK-specific antibody Ab-p48N in an immuno-complex kinase assay, confirming its identity as SIPK. The specificity of Ab-p48N had been assessed by immunoblot analysis against a panel of different MAP kinases encoded by the tobacco SIPK, WIPK, Ntf4 and NtMPK6 genes, which were expressed as His-tagged fusion proteins in E. coli. Ab-p48N recognized only the His-tagged SIPK protein (data not shown).

Figure 2A:
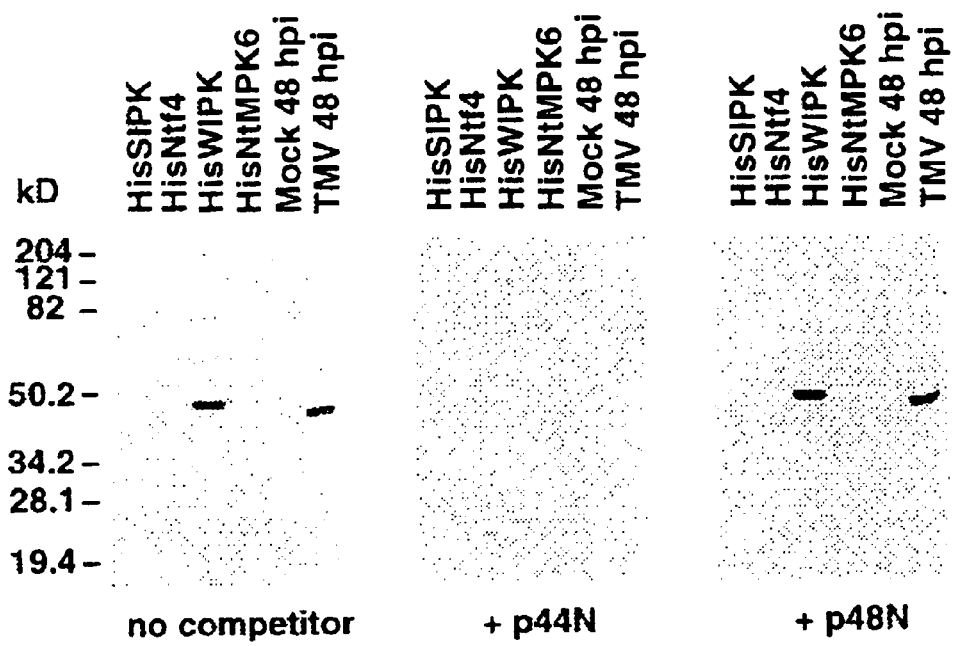
FIGS. 2A–2C. Immuno-complex kinase assays using sequence-specific antibodies against SIPK and WIPK.

The 44-kD kinase activated by TWV in encoded by WIPK. The size and substrate preference of the 44-kD kinase suggested that it also might be a MAP kinase, possibly that encoded by WIPK. To confirm or refute this possibility, antibody was prepared in rabbits against a peptide corresponding to the unique N-terminus (p44N, MADANMGAGGGQFPDFPS; SEQ ID NO: 2) of WIPK and affinity purified. The specificity of the Ab-p44N was assessed by immunoblot analysis against a panel of different MAP kinases as described above for Ab-p48N. Ab-p44N recognized only the His-tagged WIPK protein (FIG. 2A). Addition to the immuno reaction of the competitor peptide p44N, but not the p48N, blocked binding of Ab-p44N to the His-tagged WIPK protein (FIG. 2A), further demonstrating the specificity of this antibody.

Figure 2B:
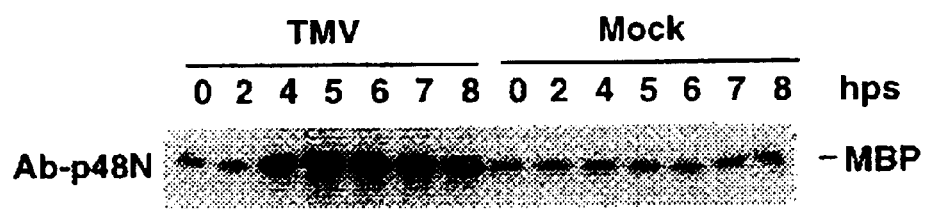
Figure 2C:
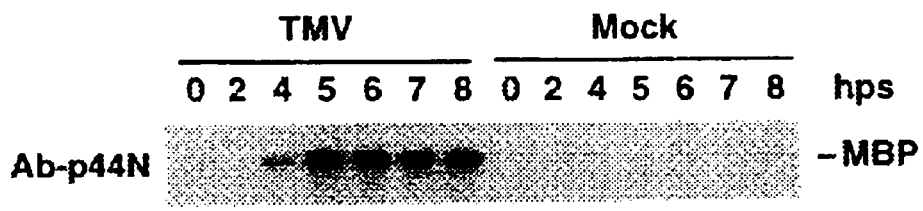

The WIPK-specific Ab-p44N was then employed to determine whether the TMV-induced 44-kD kinase activity corresponded to the WIPK-encoded protein. At various times after shifting TMV- or mock-infected plants from 32° C. to 22° C., protein extracts were prepared and subjected to an immuno-complex kinase assay (FIG. 2C). Ab-p44N immunoprecipitated a kinase whose activity correlated with the activation kinetics of the 44-kD kinase in TMV-infected plants (FIG. 1), thereby demonstrating that this kinase is encoded by WIPK. Interestingly, there was little, if any, WIPK activity in TMV-infected plants before shifting to 22° C., or in mock-infected plants before or after shifting (FIGS. 1 and 2C).

Figure 3A:
FIGS. 3A and 3B. Activation of WIPK gene expression by TMV in tobacco plants (cv Xanthi nc [NN]) after temperature shift.
Figure 3A:
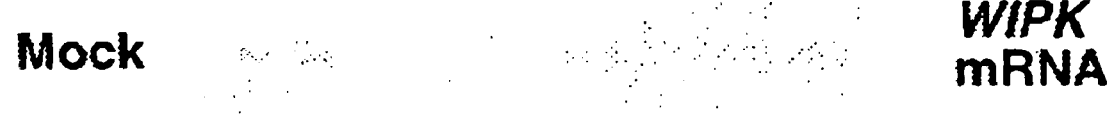
Figure 3B:
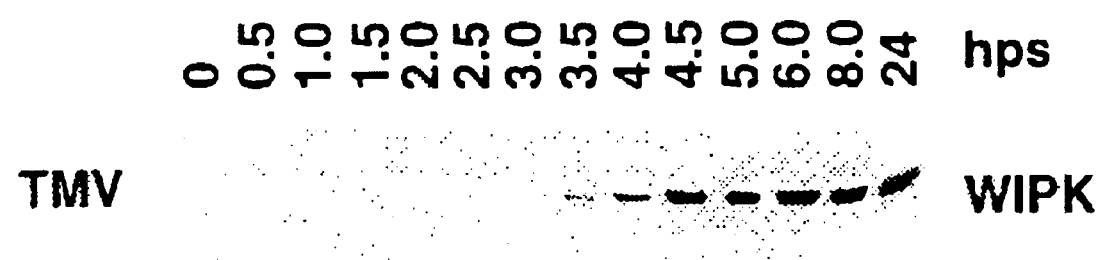
Figure 3B:
Figure 4A:
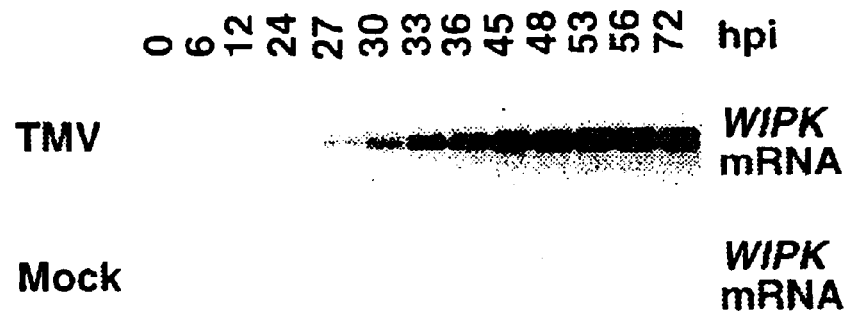
Figure 4B:
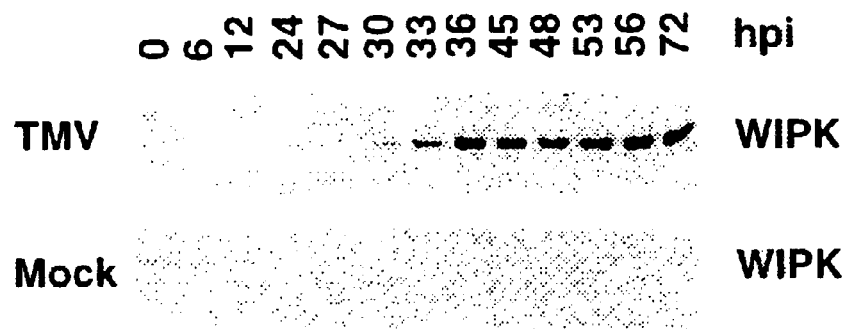
Figure 4B:
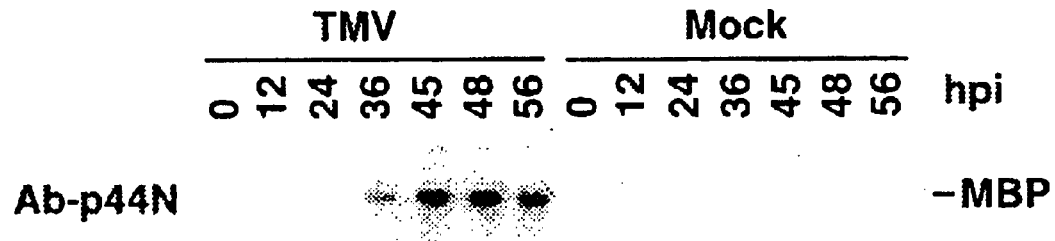

Activation of 44-kD WIPK is preceded by transcriptional activation and de novo synthesis of WIPK protein. To assess the regulation of WIPK by TMV infection, its mRNA and protein levels were monitored in the inoculated leaves of temperature-shifted tobacco plants. WIPK mRNA levels increased substantially over background by 3 hps to 22° C. and remained high at least until 8 hps before declining (FIG. 3A). Following the increases in mRNA levels, WIPK protein began to accumulate around 3.5 hps, and the levels remained elevated throughout the time course (FIG. 3B). Increases in kinase activity also correlated with the kinetics of WIPK mRNA and protein accumulation (FIGS. 1 and 3). A similarly coordinate increase in WIPK mRNA, protein and kinase activity was detected in tobacco plants infected with TMV at 22° C. and maintained at this temperature, conditions under which activation of defense responses are not blocked (FIGS. 4A–4C). These results argue that WIPK activity is regulated, at least in part, at the mRNA level. In contrast, SIPK mRNA and protein levels were not altered by TMV infection (data not shown).

Figure 5:
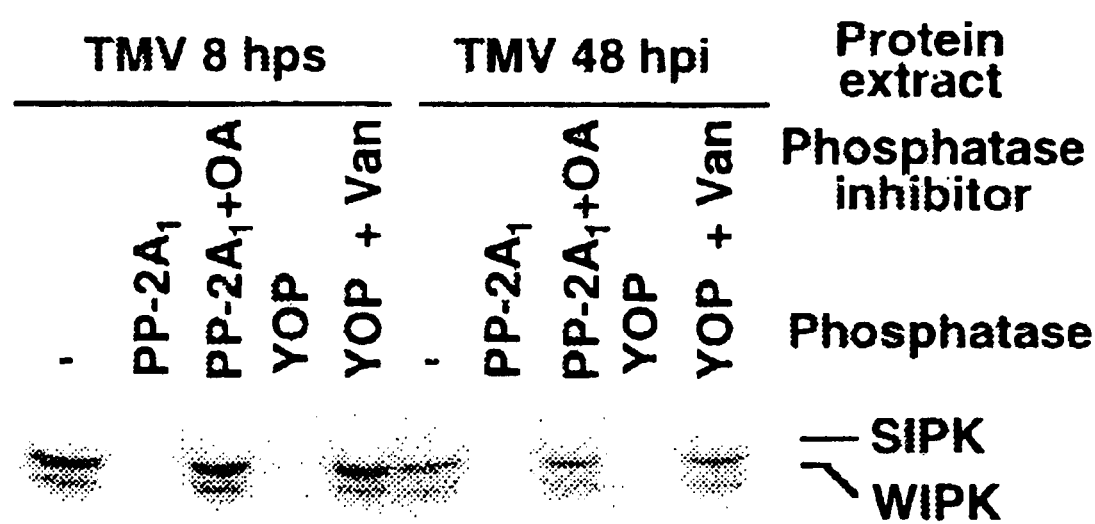
FIG. 5. Active 44-kD WIPK required both threonine and tyrosine phosphorylation. Protein extracts were prepared in the absence of phosphates inhibitors form TMV-infected leaves at 8 hr after shifting plants from 32° C. to 22° C or 48 hr after infection at 22° C. Samples containing 20 µg of protein were treated with either the serine/threonine-specific phosphatase, PP-2A$_1$ (0.25 units in 30 µL), or the tyrosine-specific protein phosphatase, YOP (2 units in 30 µL), for 20 min at 20° C. in the presence or absence of a phosphatase inhibitor. The PP-2A$_1$ inhibitor, okadaic acid (OA0, and YOP inhibitor, Na$_3$VO$_4$ (Van) were used at a concentration of 1µM and 1 mM, respectively. After phosphatase treatment, kinase activity was detected by the in-gel kinase activity assay.

Phosphorylation of tyrosine and serine/threonine is required for WIPK activity. All MAP kinases characterized thus far are activated by dual phosphorylation of a TXY motif between subdomains VII and VIII of the catalytic kinase domain. This fact, plus the observations that the WIPK-encoded 44-kD kinase activity was dramatically reduced by 24 hps compared to 8 hps (FIG. 1A) despite little, if any, change in protein level during this time period (FIG. 3B) led us to suspect that the TMV-mediated activation of WIPK is also regulated by posttranslational phosphorylation. To test this possibility, protein extracts prepared from TMV-infected plants at 8 hr after the temperature shift or at 48 hr after infection at 22° C. were treated with either the serine/threonine-specific protein phosphatase PP-2A$_1$ or the tyrosine-specific protein phosphatase YOP for 20 min before analysis by the in-gel kinase activity assay (FIG. 5). Both phosphatases inactivated the WIPK-encoded 44-kD kinase, as well as 48-kD SIPK which previously was demonstrated to be regulated by posttranslational phosphorylation (Zhang & Klessig, 1997) Furthermore, inactivation of WIPK (and SIPK) by PP-2A$_1$ and YOP could be prevented by the addition of okadaic acid, a PP-2A$_1$ inhibitor, or vanadate, a tyrosine phosphatase inhibitor.

Figure 6A:
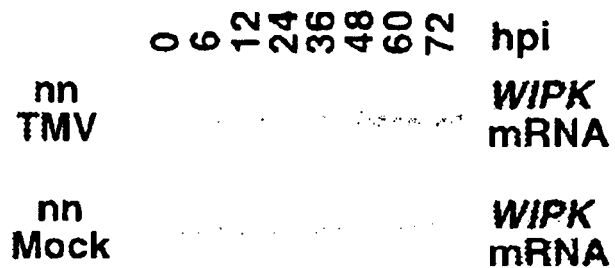
FIGS. 6A–6C. TMV activation of WIPK transcription in tobacco is N gene dependent, SA independent and systemic.
Figure 6B:

Activation of WIPK is N resistance gene dependent, SA independent and systemic. The activation of WIPK at the transcriptional and posttranslational levels only under conditions in which defense responses are induced (e.g. after transfer to 22° C.) suggests that this phenomenon is associated with resistance and may be dependent on the N resistance gene. In confirmation of this hypothesis, no increases in WIPK mRNA (FIG. 6A) or kinase activity (data not shown) were detected in TMV-infected plants from the nearly isogenic Xanthi (nn) cultivar, which lacks the N gene. Interestingly, WIPK activation at the mRNA (FIGS. 3A and 6B), protein and enzymatic activity levels (data not shown) was essentially identical in wild type Xanthi nc (NN) and transgenic Xanthi nc (NN) plants expressing the NahG gene, which encodes the SA-metabolizing enzyme salicylate hydroxylase. Thus, while many N gene-mediated defense responses are SA dependent, activation of WIPK appears to be SA independent.

Figure 6C:
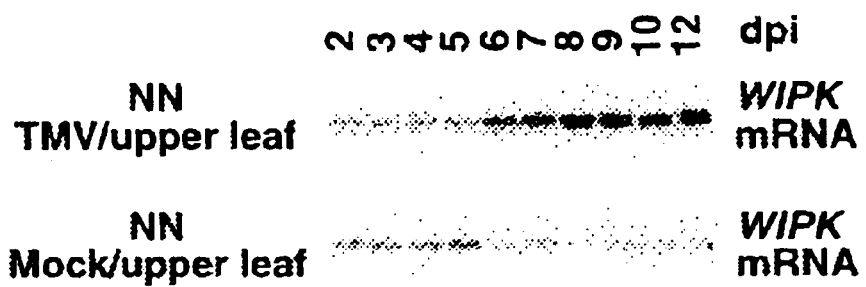

To determine whether WIPK activation is associated with SAR, another N gene-mediated phenomenon, both mRNA and protein levels were monitored in the upper uninoculated leaves of TMV-infected plants. WIPK mRNA (FIG. 6C) as well as protein (data not shown) increased over background by 6 days post inoculation (dpi). Previous analyses by others have demonstrated that SAR develops approximately 6 dpi; thus, the kinetics of WIPK induction in these uninoculated leaves is consistent with the possibility that it is involved in development of SAR.

Wounding causes increased WIPK mRNA levels, but not increased WIPK protein levels. Previous reports have shown that WIPK transcripts accumulate after wounding stress; this is the sole evidence linking WIPK to the tobacco wounding-activated kinase that phosphorylates MBP (Seo et al., 1995). To further characterize the function of WIPK in the wounding response, we tested whether increases in WIPK mRNA levels leads to an accumulation of WIPK protein.

Water infiltration and two methods of wounding (cutting and abrasion) led to only a transient elevation of WIPK mRNA levels, which was first detected approximately 20–30 minutes after wounding (FIG. 8A). The steady-state level of WIPK mRNA returned to basal level by 180 minutes after treatment.

Immunoblot analysis with the WIPK-specific antibody, Ab-p44N, demonstrated that there was little or no increase in the level of WIPK protein (FIG. 8B). More importantly, we were unable to detect the WIPK activity in protein extracts from water-infiltrated or wounded leaves (FIG. 7B). Rather, the wounding-activated kinase was immunoprecipitated by the SIPK-specific antibody, Ab-p48N (FIG. 7A). Thus, it appears that WIPK is not involved in the wounding response, even though its mRNA is transiently induced by wounding.

Discussion

The biological mechanisms of WIPK induction or WIPK activation discussed below are intended to be illustrative, and not to limit the invention in any way.

Stress-activated MAP kinases, including HOG1, SAPK/JNK and p38, have been shown to play critical roles in inducing defense responses in yeast and mammals. Similarly, various MAP kinases in plants have been shown to be activated by inducers of defense responses such as SA (Zhang & Klessig, 1997) and fungal- or bacterial-derived elicitors (Ligterink et al., 1997; Adam et al., 1997; Zhang et al., 1998). However, this is the first demonstration that activation of a plant MAP kinase is mediated by a disease resistance gene and may be involved in transmitting a signal leading to systemic, as well as local, defense responses. Furthermore, it is the first demonstration in plants, animals and microbes that activation of a MAP kinase by the same extracellular stimulus or stress requires multiple steps.

WIPK was originally isolated based on an increase in its mRNA level after wounding; it was presumed to encode a wounding-activated 46-kD MAP kinase (Seo et al., 1995). We have confirmed that wounding transiently induces WIPK at the mRNA level. However, there is little or no increase in WIPK protein following this very transient induction of WIPK mRNA. Furthermore, using the WIPK- and SIPK-specific antibodies Ab-p44N and Ab-p48N, respectively, we have discovered that the wounding-activated kinase is the 48-kD SIPK, not the 44-kD WIPK (data for SIPK set forth in Zhang & Klessig, 1998). In this regard it should be noted that the molecular weight of the wounding-activated MBP kinase described by Seo et al. (1995) (46-kD) and by the present inventors (44-kD) is not significantly different. Such slight differences in estimated molecular weight based on SDS-PAGE occurs commonly among different laboratories.

The absence of wounding-induced elevations in WIPK enzymatic activity suggests that WIPK is not involved in the wounding stress responses, despite transient mRNA induction. By contrast, during the N gene-mediated resistance response of tobacco to TMV, there is sustained induction of WIPK mRNA, followed by de novo synthesis of WIPK protein and posttranslational activation of WIPK protein by phosphorylation.

Homologs of WIPK in other plant species, including Arabidopsis Atmpk3, alfalfa MMK4 and parsley ERMK have also been shown to be induced transiently at the mRNA level by wounding, fungal elicitor or other stimuli. However, increases in protein level have never been demonstrated. In some of these cases, very rapid increases of a MBP-phosphorylating kinase activity were also observed. Even so, the relatively slow elevation of mRNA levels observed in these cases suggests that they are not directly responsible for the increases in kinase activity. One inference of our results is that these rapidly activated kinases may be encoded by SIPK functional homologs, rather than WIPK homologs.

Activation of WIPK by TMV infection was similar in wild type and NahG transgenic tobacco (FIG. 6B), suggesting that its activation is SA independent. Whether WIPK activation is mediated at a step upstream of SA in a resistance signaling pathway or is involved in a SA-independent pathway is currently unclear. However, the results of studies on transgenic tobacco constitutively expressing WIPK at the mRNA level by Seo and coworker bear on this question. After wounding, these transgenic plants had elevated levels of SA and PR proteins; these two responses are not induced by wounding in wild type plants. These results were thought to be due to altered crosstalk between wounding responses and disease defense responses in the transgenic plants. This interpretation is called into question by the discovery that the wounding-activated protein kinase is encoded by SIPK, rather than WIPK. Nonetheless, the transgenic results suggest a connection between SA/PR expression and WIPK. Assuming the transgenic plants constitutively express WIPK protein, as well as mRNA, then perhaps the upstream MAP kinase kinase (SIPK kinase) that turned on SIPK in response to wounding may also have been able to activate WIPK. If WIPK is upstream of SA in a disease resistance pathway, its activation would result in SA biosynthesis and PR gene expression. If this scenario, which is based on the assumption that the SIPK kinase is capable of activating WIPK, is correct, then what prevents inadvertent WIPK activation by wounding? In uninfected wild type plants, there is little or no WIPK protein to serve as a secondary substrate of the SIPK kinase, thereby preventing crosstalk between these two MAP kinase cascades. In other words, the multiple steps required for production of active WIPK may prevents its accidental activation.

SIPK is activated by a variety of stresses including TMV infection (FIGS. 1 and 2B), treatment with fungal elicitors (including cell wall-derived carbohydrate elicitors and elicitins from Phytophthora spp. (Zhang et al., 1998), treatment with SA (Zhang & Klessig, 1997) and wounding (Zhang & Klessig, 1998). In contrast, WIPK is activated by only a subset of these stresses including TMV infection (FIGS. 1 and 2C) and elicitin treatment (Zhang et al., 1998 and other data). Interestingly, both of these stresses lead to hypersensitive cell death. In mammals, the SAPK/JNK subfamily of MAP kinases, participates in stress-induced apoptosis. Perhaps WIPK is similarly involved in stress-induced plant cell death. Interestingly, under conditions where the same stress activates both of these kinases, their kinetics of activation are distinct. SIPK is the first to be activated, while WIPK activation is delayed. This delay probably reflects the need for transcription and de novo protein synthesis, in addition to post-translational activation of WIPK via phosphorylation.

The similarities between defense responses activated by different R gene products, as well as the conservation of structural motifs observed in these proteins, suggests that diverse plant-pathogen interactions activate a common signal transduction pathway(s) leading to disease resistance. Given that both SIPK and WIPK are activated in tobacco resisting TMV infection, it seems likely that their homologs may participate in the defense response pathway(s) initiated by R gene products found in other plant species. In addition, defense signal(s) from different R genes within a plant species, as well as non-race-specific elicitors including elicitins from Phytophthora spp, may converge on the same MAP kinase cascade(s). Determination of the role(s) of these MAP kinases in R gene-mediated defense signaling therefore should provide new opportunities for enhancing disease resistance in plants.

References

Adám, A. L., Pike, S., Hoyos, M. E., Stone, J. M., Walker, J. C. & Novacky, A. (1997) *Plant Physiol.* 115, 853–861.

An (1986) Plant Physiol., 81: 86–91.

Ausubel, F. M. et al. (eds) (1997) *Current Protocols in Molecular Biology*, John Wiley & Sons.

Bevan (1984) Nucl. Acids Res., 12: 8711–8721.

Bögre, L., Ligterink, W., Meskiene, I., Barker, P. J., Heberle-Bors, E., Huskisson, N. S. & Hirt, H. (1997) *Plant Cell* 9, 75–83.

Devereaux et al. (1984) Nucl. Acids Res. 12: 387–397.

Gelvin, Schilperoort, Verma (eds) (1993) *Plant Molecular Biology Manual*, Kluwer Academic Publishers, Dordrecht.

Gotoh, Y., Matsuda, S., Takenaka, K., Hattori, S., Iwamatsu, A., Kosako, H. & Nishida, E. (1994) *Oncogene* 9: 1891–1898.

Hirt, H. (1997) *Trends Plant Sci.* 2, 11–15.

Horsch et al., (1985) *Science* 227: 1229–1231.

Jefferson et al. (1987) *EMBO J.*, 6: 3901–3907.

Jonak, C., Kiegeri, S., Ligterink, W., Barker, P. J., Huskisson, N. S. & Hirt, H. (1996) *Proc. Natl. Acad. Sci. USA* 93, 11274–11279.

Ligterink, W., Kroj, T., zur Nieden, U., Hert, H. & Scheel, D. (1997) *Science* 276, 2054–2057.

Maliga, Klessig, Cashmore, Gruissem & Varner (eds) (1994) *Methods in Plant Molecular Biolooy—A Laboratory Manual*, Cold Spring Harbor Press.

Mansour, S. A., Matten, W. T., Hermann, A. S., Candia, J. M, Rong, S., Fukasawa, K., VandeWounde, G. F., & Ahn, N. G. (1994) *Science* 265: 966–970.

Mizoguchi, t., Irie, K., Hirayama, T., Hayashida, N., Yamaguchi-Shinozaki, K., Matsumoto, K. & Shinozaki, K. (1996) *Proc. Natl. Acad. Sci. USA* 93: 765–769.

Mizoguchi, T., Ichimura, K. & Shinozaki, K. (1997) *Trends in Biotech.* 15, 15–19.

Sambrook et al. (1989) *Molecular Cloning*, Cold Spring Harbor Laboratory.

Schuler & Zielinski (eds) (1989) *Methods in Plant Molecular Biology*, Academic Press, Inc.

Seo, S., Okamoto, M., Seto, H., Ishizuka, K., Sano, H. & Ohashi, Y. (1995) *Science* 270, 1988–1992.

Stratmann, J. W. & Ryan, C. A. (1997) *Proc. Natl. Acad. Sci. USA* 94, 11085–11089.

Suzuki, K. & Shinshi, H. (1995) *Plant Cell* 7, 639–647.

Usami, S., Banno, H., Ito, Y., Nishihama, R. & Machida, Y. (1995) *Proc. Natl. Acad. Sci. USA* 92, 8660–8664.

Weissbach & Weissbach (eds) (1988) *Methods for Plant Molecular Biology*, Academic Press, Inc.

Zhang, S., Sheng, J., Liu, Y. & Mehdy, M. C. (1993) *Plant Cell* 5, 1089–1099.

Zhang, S. & Klessig, D. F. (1997) *Plant Cell* 9, 809–824.

Zhang, S., Du, H. & Klessig, D. F. (1998) *Plant Cell* (in press).

Zhang, S. & Klessig, D. F. (1998) *Proc. Natl. Acad. Sci. USA* (submitted).

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed:

1. A method of making a transgenic plant expressing the N gene, having enhanced disease resistance comprising:

a) transforming regenerable cells of a plant with a recombinant DNA construct comprising a figwort mosaic virus 35S promoter operably linked to a nucleic acid molecule selected from the group consisting of a sequence set forth in SEQ ID NO: 1 or a sequence having 90% sequence identity therewith encoding a functional kinase enzyme, expressible in a plant; and b) regenerating transgenic plants from said transformed regenerable cells, and selecting for transgenic plants having enhanced disease resistance to a plant disease-causing agent selected from the group consisting of, tobarnoviruses, elicitin-producing fungi, parasiticein-producing fungi, cryptogein-producing fungi, harpin-producing bacteria, tobacco mosaic virus and Phytophthora fungi.

2. The method of claim 1, wherein the nucleic acid molecule is from tobacco.

3. The method of claim 1, wherein said transgenic plant is tobacco and has enhanced resistance to tobacco mosaic virus.

4. The method of claim 1, wherein said transgenic tobacco plant has enhanced resistance to species of the fungal genus Phytophthora.

5. A method of making a transgenic plant expressing the N gene, having enhanced disease resistance comprising:

a) transforming regenerable cells of a plant with a recombinant DNA construct comprising an inducible promoter operably linked to a nucleic acid molecule selected from the group consisting of a sequence set forth in SEQ ID NO: 1 or a sequence having 90% sequence identity therewith encoding a functional kinase enzyme, expressible in a plant; and b) regenerating transgenic plants from said transformed regenerable cells, and selecting for transgenic plants having enhanced disease resistance to a plant disease-causing agent selected from the group consisting of, tobamoviruses, elicitin-producing fungi, parasificein-producing fungi, cryptogein-producing fungi, harpin-producing bacteria, tobacco mosaic virus and Phytophthora fungi.

6. The method of claim 5, wherein the inducible promoter is a tetracycline repressor/operator controlled promoter.

* * * * *

SEQUENCE LISTING

<160> NUMBER OF SEQ ID NOS: 2

<210> SEQ ID NO 1
<211> LENGTH: 1725
<212> TYPE: DNA
<213> ORGANISM: Nicotiana tabacum

<400> SEQUENCE: 1

| | | | | | |
|---|---|---|---|---|---|
| tatatataca | catatgctca | tatttacact | tattacatgt | tcatatgatc | ttgtcttaat | 60 |
| taggcacata | ttttttcctt | ttcttgagct | agattaagga | ctgaaattaa | ttcatggctg | 120 |
| atgcaaatat | gggtgccggt | ggaggtcaat | tccctgattt | tccttcggtt | ttaactcacg | 180 |
| gcggacaata | tgtacagttt | gatattttg | gtaatttctt | tgagatcact | accaagtatc | 240 |
| gtcctcctat | tatgcctatt | ggtcgtggtg | cttatggaat | tgtctgctcg | gtgttgaata | 300 |
| cggagctgaa | tgagatggtt | gcagttaaga | aaatcgcgaa | tgcgtttgat | atttacatgg | 360 |
| atgctaagag | gactctccgt | gagattaagc | tcctccgcca | tttagaccat | gaaaatgtaa | 420 |
| ttggtttaag | agacgtgatt | cctccaccct | tacgaaggga | gttttctgat | gtttacattg | 480 |
| ctactgaact | catggatact | gatcttcacc | aaataattag | atccaaccaa | ggtttatcag | 540 |
| aggatcactg | tcagtacttc | atgtatcagc | tcctccgtgg | cctaaaatac | atacattccg | 600 |
| cgaatgttct | tcatagagat | ctcaaaccga | gcaaccttt | ggtaaatgca | aattgtgatc | 660 |
| ttaagatatg | tgactttggt | cttgctaggc | caaacataga | gaacgagaat | atgacggaat | 720 |
| atgttgtaac | cagatggtac | agggcaccag | agcttttgtt | gaactcttca | gattacactg | 780 |
| ctgctataga | tgtttggtct | gtcggttgca | tcttcatgga | acttatgaat | agaaaacctt | 840 |
| tgtttggtgg | aaaagatcat | gtacatcaaa | tacgcttgtt | aaccgagctt | cttggcaccc | 900 |
| caacagaagc | tgatcttggc | ttcctccaaa | atgaagatgc | aaagagatac | atcaggcaac | 960 |
| tcccacaaca | tcctcgccag | cagttagcag | aagttttccc | tcatgtgaac | ccattggcta | 1020 |
| ttgatcttgt | cgataaaatg | ttgacattcg | atcctactag | aagaattaca | gttgaggaag | 1080 |
| cattagatca | tccctacctt | gcaaagctcc | acgatgcagg | tgacgaaccg | atctgccctg | 1140 |
| ttccattctc | ctttgacttt | gagcaacaag | gaataggaga | agagcaaatt | aaggacatga | 1200 |
| tatatcagga | agctttgtca | ctgaatcctg | aatatgctta | aacataagag | aaatcaattc | 1260 |
| ttcttctcct | gtttccccctt | tgatctggag | tatctacttt | cctactgtgg | attttcttgc | 1320 |
| tcggaccgag | ccactcaatg | ttttgctca | ctggtcagtc | ctttgcgcaa | cttgtaatgt | 1380 |
| aaggcagcct | tcaatgtgca | gccatctata | tatctttttt | atttttttatt | tttattacgg | 1440 |
| tgctgtctga | gctagcttgt | gggcaccttg | attatttcat | tggatattgc | tacctcccgc | 1500 |
| cagcacaacc | atttatatct | cccactcatt | cttatgattt | gtatcttgtg | tgttgtattc | 1560 |
| agctaaaacc | aataatggca | ggttcctcaa | caatcataga | cacatcatct | atgcagaatt | 1620 |
| caagtttctc | ttttccaact | tcatcttctt | cattcatgac | ttcttcattc | actgaacttc | 1680 |
| ttgcttctga | tgattatcca | acaaagagca | aggacttgg | tgata | | 1725 |

<210> SEQ ID NO 2
<211> LENGTH: 375
<212> TYPE: PRT
<213> ORGANISM: Nicotiana tabacum

<400> SEQUENCE: 2

Met Ala Asp Ala Asn Met Gly Ala Gly Gly Gly Gln Phe Pro Asp Phe

-continued

```
  1               5              10              15
Pro Ser Val Leu Thr His Gly Gly Gln Tyr Val Gln Phe Asp Ile Phe
             20              25              30

Gly Asn Phe Phe Glu Ile Thr Thr Lys Tyr Arg Pro Pro Ile Met Pro
             35              40              45

Ile Gly Arg Gly Ala Tyr Gly Ile Val Cys Ser Val Leu Asn Thr Glu
             50              55              60

Leu Asn Glu Met Val Ala Val Lys Lys Ile Ala Asn Ala Phe Asp Ile
 65              70              75              80

Tyr Met Asp Ala Lys Arg Thr Leu Arg Glu Ile Lys Leu Leu Arg His
             85              90              95

Leu Asp His Glu Asn Val Ile Gly Leu Arg Asp Val Ile Pro Pro Pro
            100             105             110

Leu Arg Glu Phe Ser Asp Val Tyr Ile Ala Thr Glu Leu Met Asp
            115             120             125

Thr Asp Leu His Gln Ile Ile Arg Ser Asn Gln Gly Leu Ser Glu Asp
130             135             140

His Cys Gln Tyr Phe Met Tyr Gln Leu Leu Arg Gly Leu Lys Tyr Ile
145             150             155             160

His Ser Ala Asn Val Leu His Arg Asp Leu Lys Pro Ser Asn Leu Leu
            165             170             175

Val Asn Ala Asn Cys Asp Leu Lys Ile Cys Asp Phe Gly Leu Ala Arg
            180             185             190

Pro Asn Ile Glu Asn Glu Asn Met Thr Glu Tyr Val Val Thr Arg Trp
            195             200             205

Tyr Arg Ala Pro Glu Leu Leu Leu Asn Ser Ser Asp Tyr Thr Ala Ala
210             215             220

Ile Asp Val Trp Ser Val Gly Cys Ile Phe Met Glu Leu Met Asn Arg
225             230             235             240

Lys Pro Leu Phe Gly Gly Lys Asp His Val His Gln Ile Arg Leu Leu
            245             250             255

Thr Glu Leu Leu Gly Thr Pro Thr Glu Ala Asp Leu Gly Phe Leu Gln
            260             265             270

Asn Glu Asp Ala Lys Arg Tyr Ile Arg Gln Leu Pro Gln His Pro Arg
            275             280             285

Gln Gln Leu Ala Glu Val Phe Pro His Val Asn Pro Leu Ala Ile Asp
290             295             300

Leu Val Asp Lys Met Leu Thr Phe Asp Pro Thr Arg Arg Ile Thr Val
305             310             315             320

Glu Glu Ala Leu Asp His Pro Tyr Leu Ala Lys Leu His Asp Ala Gly
            325             330             335

Asp Glu Pro Ile Cys Pro Val Pro Phe Ser Phe Asp Phe Glu Gln Gln
            340             345             350

Gly Ile Gly Glu Glu Gln Ile Lys Asp Met Ile Tyr Gln Glu Ala Leu
            355             360             365

Ser Leu Asn Pro Glu Tyr Ala
370             375
```